United States Patent [19]

Okutani

[11] Patent Number: 4,536,504
[45] Date of Patent: Aug. 20, 1985

[54] HEXAHYDRODIOXOPYRIMIDINES, THEIR PRODUCTION AND USE

[75] Inventor: Tetsuya Okutani, Osaka, Japan

[73] Assignee: Takeda Chemical Industries, Ltd., Doshomachi, Japan

[21] Appl. No.: 513,339

[22] Filed: Jul. 13, 1983

[30] Foreign Application Priority Data

Jul. 13, 1982 [JP]  Japan ................ 57-122535

[51] Int. Cl.³ .................. A61K 31/515; C07D 239/20
[52] U.S. Cl. ..................................... 514/270; 544/300
[58] Field of Search ................ 542/416; 424/251; 544/300

[56] References Cited

U.S. PATENT DOCUMENTS 4,190,656  2/1980  Matsumura et al. ............... 424/251

Primary Examiner—Donald G. Daus
Assistant Examiner—Stephen M. Kapner
Attorney, Agent, or Firm—Wegner & Bretschneider

[57] ABSTRACT

Novel compounds of the formula:

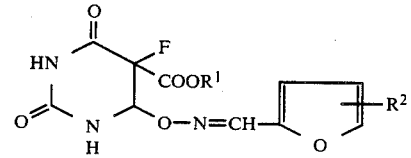

wherein $R^1$ is lower alkyl; $R^2$ is hydrogen or lower alkyl, which are produced by reacting a compound of the formula:

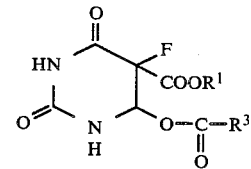

wherein $R^3$ is hydrocarbon residue, with a compound of the formula:

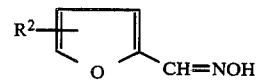

The novel compounds have antiviral and antibacterial activity, and are useful to prolong the life span of tumor-bearing warm-blooded animals.

15 Claims, No Drawings

HEXAHYDRODIOXOPYRIMIDINES, THEIR PRODUCTION AND USE

The present invention relates to novel hexahydrodioxipyrimidines, their production and use.

In more particular, the present invention is concerned with hexahydrodioxopyrimidines of the formula:

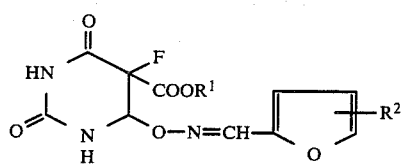
[I]

wherein $R^1$ is lower alkyl; $R^2$ is hydrogen or lower alkyl, and with antitumor agents which contain the compounds of the formula [I].

The hexahydrodioxopyrimidines according to this invention are useful compounds which prolong the life span of tumor-bearing warm-blooded animals and have antiviral and antibacterial activity.

It is an object of this invention to provide the compounds of the formula [I] and method for producing thereof.

Other objects will be made clear from the description appearing hereinafter.

6-(Mono-substituted-methyleneaminooxy)-5-fluoro-5-alkoxycarbonyl-5,6-dihydrouracils (hereinafter referred to briefly as "methyleneaminoxydihydrouracils") are the compounds which have been described in the Patent Gazette as the Japanese Unexamined Published Patent Application No. 46791/1979 and U.S. Pat. No. 4,190,656. The present inventor, after intensive investigation of these compounds, found that the 6-(furfurylideneamonooxy)-5-fluoro-5-alkoxycarbonyl-5,6-dihydrouracils as represented by the above formula [I] which have not been specifically disclosed in the said Patent Gazette possess by far improved antitumor activity as compared with other methyleneaminoxydihydrouracils, and the finding has culminated in the present invention.

With reference to the above formula [I], the lower alkyl groups represented by $R^1$ and $R^2$ may each be the same as, or different from, the other, and their examples include alkyl groups of 1 to 6 carbon atoms (e.g., methyl, ethyl, propyl, isopropyl, butyl, isobutyl, sec-butyl, tert-butyl, pentyl, isopentyl, hexyl). The compound of the formula [I] wherein $R^1$ is alkyl of 2 to 4 carbon atoms and $R^2$ is hydrogen is desirable for the objects of the present invention.

With the compounds [I], there exist cis- and trans-stereoisomers with respect to furfurylideneamionooxy group at the 6- position and fluorine atom or alkoxycarbonyl group at the 5-position, and such individual isomers as well as mixtures thereof are understood to be included in the scope of the compounds [I] according to the present invention, as well.

The compounds [I] of the present invention can be produced for example by reacting a compound of the formula:

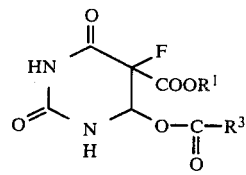
[II]

wherein $R^1$ is as defined hereinbefore; $R^3$ is hydrocarbon residue, with a compound of the formula:

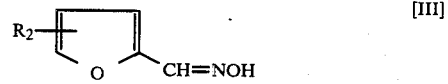
[III]

wherein $R^2$ is as defined hereinbefore. Also, the compounds [I] can be produced by reacting an intermediate of the formula:

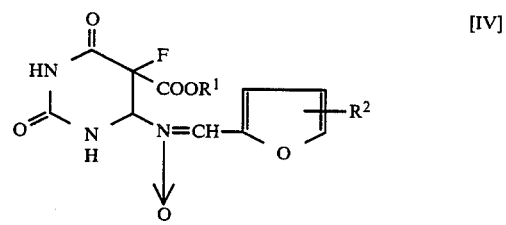
[IV]

wherein $R^1$ and $R^2$ are as defined hereinbefore, which may in certain instances be formed from the compounds [II] and [III], further with the corresponding compound [III] after or without being isolated, or by allowing a compound [IV] as such to undergo rearrangement.

Examples of the hydrocarbon residue represented by $R^3$ include lower alkyl groups of 1 to 4 carbon atoms (e.g., methyl, ethyl, etc.), mono-, di- or tri-halogeno lower alkyl groups of 1 to 4 carbon atoms (e.g., mono-, di- or trichloromethyl, trifluoromethyl, etc.) and the phenyl group.

With the compounds [III], there exist cis (Z)- and trans (E)-stereoisomers, and the above formula [III] is understood to include each of their isomers or mixtures thereof.

It is advantageous to use the compound [III] in a ratio ranging from 1 to 2 moles against 1 mole of the compound [II] and in a ratio within the range of a catalytic amount to 2 moles against 1 mole of the compound [IV].

This reaction may be conducted at a suitable temperature in the range of a temperature under ice-cooling to about 100° C. for about 5 to about 72 hours.

This reaction is carried out in the presence of an appropriate solvent such as ketones (e.g., acetone, methyl ethyl ketone, etc.), esters (e.g., ethyl acetate, butyl acetate, etc.), ethers (e.g., tetrahydrofuran, dioxane, 1,2-dimethoxyethane, etc.), dimethylformamide or a suitable solvent mixture thereof, whereby in particular, the use of ketones, desirably acetone, can produce satisfactory results. In addition, the catalysts to be described below can be employed with an aim to allowing them to act as solvent or as a mixture with the above solvents.

In some instances, this reaction can be advantageously carried out, for example, by use of tertiary amines (e.g., pyridine, picoline, triethylamine, dimethylaniline, etc.) as catalyst.

Referring more particlarly to this reaction, when the compounds [II] are reacted with (E)-furfuraldoximes denoted by the compounds [III] in pyridine-acetone in the presence of triethylamine at 0° to 40° C., preferably at room temperature, 6-[(E)-furfurylideneaminooxyl]-5-fluoro-5-alkoxycarbonyl-5,6-dihydrouracils (hereinafter referred to briefly as "(E)-furfurylideneaminooxydihydrouracils"]-5-fluoro-5-alkoxydenoted by the compounds [I] can be produced in the purity of not less than 90%, along with 6-[(Z)-furfurylideneaminooxy]-5-fluoro-5-alkoxycarbonyl-5,6-dihydrouracils (hereinafter referred to briefly as "(Z)-furfurylideneaminooxydihydrouracils") as by-products being normally formed in small amounts. When the compounds [II] are reacted with (Z)-furfuraldoximes denoted by the compounds [III] in pyridine-acetone at 50° to 70°C., besides, 6-[(Z)-furfurylideneaminooxydihydrouracils] denoted by the compounds [I] can be produced in the purity of not less than 90%, along with (E)-furfurylideneaminooxydihydrouracils denoted by the compounds [I] as by-products being normally formed in small amounts.

When the compounds [II] are reacted with (Z)-furfuraldoximes denoted by the compounds [III] in pyridineacetone at a temperature ranging from a temperature under ice-cooling to 40° C., preferably at room temperature or lower temperature, moreover, nitrones denoted by the compounds [IV] are yielded as the main product, and the compounds [IV] can be warmed in pyridine-acetone at 50° to 70° C. or reacted with the (Z)-furfuraldoximes denoted by the compounds [III] under the same reaction conditions to produce the (Z)-furfurylideneaminooxydihydrouracils denoted by the compounds [I] in the purity of not less than 85%. When the compounds [IV] are reacted with the (E)-furfuraldoximes denoted by the compounds [III] in pyridine-acetone at 0° to 40° C., desirably at room temperature or lower temperature, further the (E)-furfurylideneaminooxydihydrouracils denoted by the compounds [I] can be produced in the purity of not less than 90%.

The compounds [I] as produced in the above-mentioned manner can be easily isolated and purified by suitably employing treatment procedures known per se (e.g. extraction, concentration, recrystallization, chromatography, etc.).

The compounds [II] to be used in the above reactions can be produced for example by the procedure as disclosed in the Patent Gazette as the Japanese Unexamined Published Patent Application No. 46791/1979. On the occasion of carrying out the said reaction, nevertheless, the resultant reaction mixture as such, without isolating the compounds [II], may be reacted with the compound [III] to produce the compounds [I], and may also be allowed to pass via the compound [IV] to produce the compounds [I].

The compounds [I] of the present invention, possessing outstandingly excellent antitumor effect as compared with other methyleneaminooxydihydrouracils, inhibit growth of tumor cells and manifest the remarkable life-spanprolongation effect toward tumor-bearing warm-blooded animals. Consequently, the compounds [I] are of value as an antitumor agent against various solid cancers (e.g., gastrointestinal tract cancers, lung cancer, mammary cancer, urinary tract cancer, etc.).

The compounds show the relatively low toxicity, and in the case of being used as the above antitumor agent, can be safely administered as such or as formulated by preparation methods known per se with pharmacologically acceptable carriers, excipients or diluted into pharmaceutical compositions such as powders, granules, tablets, capsules, dry syrups, solutions, suppositories, injections, etc., either orally or parenterally. The compounds, even when administered orally, display improved bioavailability and exhibit greater rate of biotransformation into 5-fluorouracil (5-FU), as well.

The dosage can be suitably decided depending upon diseases, symptons, kind of compounds, route of administration, etc. In the case of oral administration to a patient with gastrointestinal tract cancer, for example, dosage is desirably in the range of about 2 to 20 mg/kg body weight as the compound [I] as a single dose, usually about 1 to 3 times daily.

When the compounds [I] of the present invention are employed as antitumor agent, furthermore, they may be used in combination with other antitumor agents or may be utilized in conjunction with antitumor synergistic agents (e.g., uracil, pyrimidine, etc.), as the case may be.

The examples, experiment examples and preparation example are described below to illustrate the present invention more specifically, but the scope of the present invention is not understood to be limited by these examples.

EXAMPLE 1

In 450 ml of pyridine-acetone (pyridine:acetone=2:1) were dissolved 131 g (0.5 mol) of ethyl 5-fluoro-6-acetoxy-1,2,3,4,5,6-hexahydro-2,4-dioxopyrimidine-5-carboxylate and 66.5 g (0.6 mol) of (Z)-furfuraldoxime, and the solution was stirred at 60° C. for 15 hours. The solvent was evaporated under reduced pressure, and the residual oily material was poured into 3 l of ice-cooled water, and crystals precipitated were collected by filtration. The crystals were washed with water (500 ml×2), dried under reduced pressure and recrystallized from ethanol and then from ethyl acetate-hexane (7:3) to yield 63.5 g of ethyl 5-fluoro-6-(Z)-furfurylideneaminooxy-1,2,3,4,5,6-hexahydro-2,4-dioxopyrimidine-5carboxylate. m.p. 152°-153° C.

NMR spectrum (90 MHz, DMSO-$d_6$)$\delta$: 1.23(3H, t, J=7 Hz), 4.32(2H, q, J=7 Hz), 5.67(1H, dxd, J=5 Hz and 1Hz), 6.68(1H, dxd, J=4 Hz and 2 Hz), 7.03(1H, d, J=4 Hz), 7.83(1H, s), 7.87(1H, d, J=2 Hz), 9.20(1H, broad), 11.20(1H, s)

Elemental analysis, for $C_{12}H_{12}FN_3O_6$ Calcd.: C, 46.01; H, 3.86; N, 13.42; Found : C, 46.06; H, 3.86; N, 13.46.

EXAMPLE 2

In 20 ml of pyridine were dissolved 5.24 g (20 mmol) of ethyl 5-fluoro-6-acetoxy-1,2,3,4,5,6-hexahydro-2,4-dioxopyrimidine-5-carboxylate and 2.62 g (23.6 mmol) of (E)-furfuraldoxime, and 2.02 g (20 mmol) of triethylamine was added to the solution, followed by stirring at room temperature for 15 hours. The reaction solution was poured into 200 ml of ice-cooled water, and crystals precipitated were collected by filtration and washed with water. The crystals were dried under reduced pressure and recrystallized from ethanol to give 3.28 g of ethyl 5-fluoro-6-(E)-furfurylideneaminooxy-1,2,3,4,5,6-hexahydro-2,4-dioxopyrimidine-5-carboxylate. m.p. 189°-190° C.

NMR spectrum (90 MHz, DMSO-$d_6$)$\delta$: 1.23(3H, t, J=7 Hz), 4.30(2H, q, J=7 Hz), 5.57(1H, dxd, J=5 Hz and 1 Hz), 6.60(1H, dxd, J=4 Hz and 2 Hz), 6.85 (1H, d, J=4 Hz), 7.82(1H, d, J=2 Hz), 8.27(1H, s), 9.10(1H, m), 11.17(1H, s).

Elemental analysis, for $C_{12}H_{12}FN_3O_6$ Calcd.: C, 46.01; H, 3.86; N, 13.42; Found : C, 46.17; H, 3.69; N, 13.55.

EXAMPLE 3

In 75 ml of pyridine-acetone (pyridine:acetone=2:1) were dissolved 20 g (76 mmol) of ethyl 5-fluoro-6-acetoxy-1,2,3,4,5,6-hexahydro-2,4-dioxopyrimidine-5-carboxylate and 11.4 g (91 mol) of (Z)-5-methylfuraldoxime, and the solution was stirred at room temperature for 4 days. The reaction solution was concentrated under reduced pressure, and the residue was treated with water. Crystals precipitated were collected by filtration and washed with water. The crystals were dried under reduced pressure and dissolved in acetone, and insoluble matters were filtered off. The filtrate was concentrated, and the residue was chromatographed on silica gel with chloroform-acetone (7:1), followed by recrystallization from ethyl acetate-hexane to yield 4.6 g of ethyl 5-fluoro-6-[(Z)5-methylfurfurylideneaminooxy]-1,2,3,4,5,6-hexahydro-2,4-dioxopyrimidine-5-carboxylate. m.p. 163°–164° C.

NMR spectrum (90 MHz, DMSO-$d_6$)δ: 1.23(3H, t, J=7 Hz), 2.30(3H, s), 4,30(2H, q, J=7 Hz), 5.60(1 H, dxd, J=5 Hz and 1.5 Hz), 6.30(1H, d, J=4 Hz), 6.90(1H, d, J=4 Hz), 7.70(1 H, s), 9.13(1H, m), 11.13(1H, s).

Elemental analysis, for $C_{13}H_{14}FN_3O_6$ Calcd.: C, 47.71; H, 4.31; N, 12.84; Found: C, 47.81; H, 4.27; N, 12.85.

EXAMPLE 4

In 45 ml of pyridine-acetone (pyridine:acetone=2:1) were dissolved 11.6 g (40 mmol) of isobutyl 5-fluoro-6-acetoxy-1,2,3,4,5,6-hexahydro-2,4-dioxopyrimidine-5-carboxylate and 6.1 g (54.9 mmol) of (Z)-furfuraldoxime, and the solution was stirred at 60° C. for 16 hours. The solvent was distilled off under reduced pressure, and the residue was dissolved in 150 ml of ethyl acetate. The solution was washed three times with 50-ml portions of water, and the ethyl acetate layer was dried and the solvent was evaporated under reduced pressure. The residue was recrystallized three times from ethyl acetate-hexane to give 5.5 g of isobutyl 5-fluoro-6-(Z)-furfurylideneaminooxy-1,2,3,4,5,6-hexahydro-2,4-dioxopyrimidine-5-carboxylate. m.p. 159°–160° C.

NMR spectrum (90 MHz, DMSO-$d_6$)δ: 0.89(6H, d, J=7 Hz), 1.70–2.15(1H, m), 4.09(2H, d, J=7 Hz), 5.66(1H, dxd, J=5 Hz and 2 Hz), 6.70(1H, dxd, J=4 Hz and 2 Hz), 7.05(1H, d, J=4 Hz), 7.83(1H, s), 7.88(1H, d, J=2 Hz), 9.22(1H, broad), 11.22(1H, s).

Elemental analysis, for $C_{14}H_{16}FN_3O_6$ Calcd.: C, 49.27; H, 4.73; N, 12.31; Found: C, 49.00; H, 4.74; N, 12.24.

EXAMPLE 5

In 10 ml of pyridine were dissolved 2.9 g (10 mmol) of isobutyl 5-fluoro-6-acetoxy-1,2,3,4,5,6-hexahydro-2,4-dioxopyrimidine-5-carboxylate and 2.22 g (20 mmol) of (E)-furfuraldoxime, and 1.01 g (10 mmol) of dried triethylamine was added to the solution, followed by stirring at room temperature for 21 hours. The reaction solution was concentrated under reduced pressure, and 50 ml of ethyl acetate was added to the residue. The organic layer was washed three times with 10-ml portions of water, and the solvent was dried and evaporated under reduced pressure. The residue was recrystallized twice from ethyl acetate-hexane to give 2.39 g of isobutyl 5-fluoro-6-(E)-furfurylideneaminooxy-1,2,3,4,5,6-hexahydro-2,4-dioxopyrimidine-5-carboxylate. m.p. 167°–168° C.

NMR spectrum (90 MHz, DMSO-$d_6$)δ: 0.89(6 H, d, J=7 Hz), 1.70–2.07(1H, m), 4.07(2H, d, J=6 Hz), 5.60(1H, dxd, J=5 Hz and 1 Hz), 6.61(1 H, dxd, J=3 Hz and 2 Hz), 6.87(1 H, d, J=3 Hz), 7.83(1H, d, J=2 Hz), 8.23(1H, broad), 11.19(1H, s).

Elemental analysis, for $C_{14}H_{16}FN_3O_6$ Calcd.: C, 49.27; H, 4.73; N, 12.31; Found: C, 49.36; H, 4.94; N, 12.42.

EXAMPLE 6

In 70 ml of pyridine were dissolved 18.3 g (70 mmol) of ethyl 5-fluoro-6-acetoxy-1,2,3,4,5,6-hexahydro-2,4-dioxopyrimidine-5-carboxylate and 13.1 g (105 mmol) of (E)-5-methylfurfuraldoxime (containing 13% of the Z form), and 7.07 g (70 mmol) of triethylamine was added to the solution, followed by stirring at room temperature for 15 hours. The reaction solution was poured into 500 ml of ice-cooled water, and crystals precipitated were collected by filtration and washed with water. The crystals were dried under reduced pressure ($P_2O_5$) and recrystallized from 170 ml of ethanol to give 11.8 g of ethyl 5-fluoro-6-[(E)-5-methylfurfurylideneaminooxy]-1,2,3,4,5,6-hexahydro-2,4-dioxopyrimidine-5-carboxylate. m.p. 181°–182° C.

NMR spectrum (90 MHz, DMSO-$d_6$)δ: 1.23(3H, t, J=7 Hz), 2.30(3H, s), 4.30(2H, q, J=7 Hz), 5.52(1H, dxd, J=5 Hz and 1.5 Hz), 6.22(1H, d, J=4 Hz), 6.72(1H, d, J=4 Hz), 8.13(1H, s), 9.07(1H, m), 11.10(1H, s).

Elemental analysis, for $C_{13}H_{14}FN_3O_6$ Calcd.: c, 47.71; H, 4.31; N, 12.84; Found: C, 47.74; H, 4.33; N, 12.87.

EXAMPLE 7

In 60 ml of pyridine-acetone (pyridine:acetone=2:1) were dissolved 26.2 g (0.1 mol) of ethyl 5-fluoro-6-acetoxy-1,2,3,4,5,6-hexahydro-2,4-dioxopyrimidine-5-carboxylate and 13.33 g (0.12 mol) of (Z)-furfuraldoxime, and the solution was stirred at room temperature for 73 hours. The solvent was distilled off under reduced pressure, and the residue was treated with 150 ml of water, followed by stirring. The separated viscous solid was recovered by filtration, and washed with water. The solid was added to 50 ml of ethyl acetate, and crystals precipitated were collected by filtration to give 11.27 g of N-(furfurylidene)-5-(5-fluoro-5-ethoxycarbonyl-1,2,3,4,5,6-hexahydro-2,4-dioxopyrimidine-6-yl)amine-N-oxide. m.p. 136°–137° C.

NMR spectrum (90 MHz, DMSO-$d_6$)δ: 1.23(3H, , J=7 Hz), 4.31(2H, q, J=7 Hz), 6.02(1H, dxd, J=1 Hz, J=4 Hz), 6.67(1H, broad), 7.60(1H, d, J=4 Hz), 7.88(1H, d, J=2 Hz), 8.30(1H, broad), 11.01(1H, s).

Elemental analysis, for $C_{12}H_{12}N_3O_6F$ Calcd: C, 46.01; H, 3.86; N, 13.42; Found: C, 46.00; H, 3.82; N, 13.22.

The filtrate was concentrated under reduced pressure, and the residue was purified by silica gel column chromatography with ethyl acetate-hexane (1:1) to yield 5 g of ethyl 5-fluoro-6-(Z)-furfurylideneaminooxy-1,2,3,4,5,6-hexahydro-2,4-dioxopyrimidine-5-carboxylate.

EXAMPLE 8

To 57 ml of pyridine-acetone (pyridine:acetone=9:10) were added 18.64 g (64.2 mmol) of isobutyl 5-fluoro-6-acetoxy-1,2,3,4,5,6-hexahydro-2,4-dioxopyrimidine-5-carboxylate and 8.56 g (77.1 mmol) of (Z)-furfuraldoxime, and the solution was stirred at room temperature for 72 hours. The solvent was distilled off under reduced pressure, and the residue was treated with acetone. Crystals precipiated were collected by filtration and washed with acetone, followed by recrystallization from ethyl acetate to yield 6.54 g of N-(furfurylidene)-(5-fluoro-5-iosbutoxycarbonyl-1,2,3,4,5,6-hexahydro-2,4-dioxopyrimidine-6-yl)amine N-oxide. m.p. 162°–164° C.

NMR spectrum (90 MHz, DMSO-$d_6$)$\delta$: 0.90(6H, d, J=7 Hz), 1.73–2.17(1H, m), 4.11(2H, d, J=6 Hz), 6.07(1H, dxd, J=1 Hz, J=5 Hz), 6.71(1H, q), 7.65(1H, d, J=4 Hz), 7.90(1H, d, J=2 Hz), 8.35(1H, s), 8.87(1H, broad), 11.09(1H, s).

Elemental analysis, for $C_{14}H_{16}N_3O_6F$ Calcd.: C, 49.27; H, 4.73; N, 12.31; Found: C, 48.86; H, 4.77; N, 11.25.

EXAMPLE 9

In 3 ml of pyridine-acetone (pyridine:acetone=2:1) were dissolved 341 mg (1 mmol) of N-(furfurylidene)-(5-fluoroisobutoxycarbonyl-1,2,3,4,5,6-hexahydro-2,4-dioxopyrimidine-6-yl)-amine N-oxide and 133 mg (1.2 mmol) of (Z)-furfuraldoxime, and the solution was stirred at 60° C. for 15 hours. The solvent was distilled off under reduced pressure, and the residue was purified by silica gel column chromatography with hexane-ethyl acetate (4:1), followed by recrystallization from ethyl acetate-hexane (2:1) to yield 193 mg of isobutyl 5-fluoro-6-[(Z)-furfurylideneaminooxy]-1,2,3,4,5,6-hexahydro-2,4-dioxopyrimidine-5-carboxylate.

EXAMPLE 10

In 3 ml of pyridine-acetone (pyridine-acetone=2:1) were dissolved 341 mg (1 mmol) of N-(furfurylidene)-(5-fluoro-5-isobutoxycarbonyl-1,2,3,4,5,6-hexahydro-2,4-dioxopyrimidine-6-yl)amine N-oxide and 133 mg (1.2 mmol) of (E)-furfuraldoxime, and the solution was stirred at room temperature for 51 hours. The reaction solution was treated in the same manner as described in Example 9 to give 188 mg of isobutyl 5-fluoro-6-[(E)-furfurylideneaminooxy]-1,2,3,4,5,6-hexahydro-2,4-dioxopyrimidine-5-carboxylate.

EXAMPLE 11

In 1.5 ml of pyridine-acetone (pyridine:acetone=2:1) was dissolved 100 mg (0.29 mmol) of N-(furfurylidene)-(5-fluoro-5-isobutoxycarbonyl-1,2,3,4,5,6-hexahydro-2,4-dioxopyrimidine-6-yl)amine N-oxide, and the solution was stirred at 60° C. for 15 hours. The reaction solution was treated in the same manner as described in Example 9 to give 24 mg of isobutyl 5-fluoro-6-[(Z)-furfurylideneaminooxy]-1,2,3,4,5,6-hexahydro-2,4-dioxopyrimidine-5-carboxyalte.

EXAMPLE 12

In 50 ml of acetone was dissolved 20.0 g (85.4 mmol) of isopropyl 5-fluoro-6-hydroxy-1,2,3,4,5,6-hexahydro-2,4-dioxopyrimidine-5-carboxylate, and 8.78 g (111.0 mmol) of pyridine and 8.65 g (93.9 mmol) of acetic anhydride were added to the solution, followed by stirring under ice-cooling for 3 hours and subsequently at room temperature for 16 hours. The solvent was disttiled off under reduced pressure, and the acetylated compound, which precipitates after the addition of water, was recovered by filtration, washed with water and dried. One-half its amount and 5.70 g (51.2 mmol) of (Z)-furfuraldoxime were dissolved in 30 ml of pyridineacetone (pyridine:acetone=2.1), and the solution was stirred at 60° C. for 15 hours. The solvent was distilled off under reduced pressure, and the residue was purified by silica gel column chromatography with hexane-ethyl acetate changing gradually the mixing ratio from (9:1) to (1:2) to yield 5.5 g of 5-fluoro-6-[(Z)-furfurylideneaminooxy]-5-isopropyloxycarbonyl-1,2,3,4,5,6-hexahydro-2,4-dioxopyrimidine. m.p. 131°–134° C.

NMR spectrum (90 MHz, DMSO-$d_6$)$\delta$: 1.25(6H, d, J=6 Hz), 5.08(1H, m, J=6 Hz), 5.55(1H, dxd, J=1 Hz, J=5 Hz), 6.67 (1H, q), 7.01(1H, d, J=4 Hz), 7.81(2H, m), 9.08(1H, broad), 11.10(1H, s).

EXAMPLE 13

In 30 ml of pyridine-acetone (pyridine:acetone=2:1) were dissolved one-half amont of the acetylated compound as obtained on the way of Example 12 and 5.70 g (51.2 mmol) of (E)-furfuraldoxime, and the solution was stirred at room temperature for 95 hours. The reaction solution was treated in the same manner as described in Example 12 to yield 6.1 g of 5-fluoro-6-[(E)-furfurylideneaminooxy]-5-isopropyloxycarbonyl-1,2,3,4,5,6-hexahydro-2,4-dioxopyrimidine. m.p. 185°186° C. P NMR spectrum (90 MHz, DMSO-$d_6$)$\epsilon$: 1.25(6H, d, J=6 Hz), 5.07(1H, m, J=6 Hz), 5.48(1H, dxd, J=1 Hz, J=5 Hz), 6.58(1H, q), 6.83(1H, d, J=4 Hz), 7.80(1H, d, J=1 Hz), 8.25(1H, s), 9.06(1H, dxd, J=5 Hz, J=3 Hz), 11.10(1H, s).

Experiment Example 1

Antitumor effect against mouse myeloma MOPC-104E. [Experimental procedure]

$1\times10^6$ cells of the above tumor were transplanted into BALB/c female mice under the axillary skin, and the drug substance was administered orally, once a day for 7 consecutive days after 24 hours had elapsed. On day 10 after the tumor had been transplanted, tumor weights were measured and antitumor effects were expressed in the ratio (T/C %) of the average tumor weight (T) for the treated group (a group consisting of 5 animals) to the average tumor weight (C) for the control group (15 animals).

[Results]

TABLE 1

| Test Compound | Dosage (mM/kg) | T/C (%) |
|---|---|---|
| Compound of Example 1 | 0.25 | 21 |
| | 0.5 | 3 |
| | 1 | 0 |
| Compound of Example 2 | 0.25 | 28 |
| | 0.5 | 2 |
| | 1 | 0 |
| Ethyl 5-fluoro-6-(α-methyl)furfurylideneaminoxy-1,2,3,4,5,6-hexahydro-2,4-dioxopyrimidine-5-carboxylate | 0.25 | 44 |
| | 0.5 | 15 |
| | 1 | 2 |

As may be obvious from the above results, the compounds of the present invention, in terms of equimolar dose, exhibited the inhibitory effect against tumor multiplication superior to that of ethyl 5-lfluoro-6-(α-methyl)-furfurylideneaminooxy-1,2,3,4,5,6-hexahydro- 2,4-dioxopyrimidine-5-carboxylate as described in the Japanese Unexamined Published Patent Application No. 46791/1979.

Experiment Example 2

Using the compounds of Examples 4 and 5, the antitumor effects against mouse myleoma MOPC-104E were tested by the similar experiment procedure as shown in Experiment Example 1.

The results were shown in Table 2.

TABLE 2

| Test Compound | Dosage (mM/kg) | T/C (%) |
|---|---|---|
| Compound of Example 4 | 0.25 | 23 |
|  | 0.5 | 5 |
|  | 1 | 0 |
| Compound of Example 5 | 0.25 | 19 |
|  | 0.5 | 4 |
|  | 1 | 0 |

Experiment Example 3

Effect on the growth of subcutaneously transplanted Colon 26 carcinoma.

[Experimental procedure]

Small fragments of tumor were transplanted subcutaneously into CDF$_1$/Crj male mice by trocar on Day 0. Drugs were administered orally to mice for daily 7 consecutive days starting 24 hours after tumor transplantation. Mice were sacrificed on Day 10. The antitumor effects were expressed in the ratio (T/C %) of the average tumor weight (T) for the treated group (a group consisting of 5 animals) to the average tumor weight (C) for the control group (20 animals).

[Results]

TABLE 3

| Test Compound | Dosage (mM/kg) | T/C (%) |
|---|---|---|
| Compound of Example 4 | 0.25 | 19 |
|  | 0.5 | 0 |
|  | 1 | 0 |
| Compound of Example 5 | 0.25 | 50 |
|  | 0.5 | 11 |
|  | 1 | 2 |
| Ethyl 5-fluoro-6-(α-methyl)furfurylideneaminooxy-1,2,3,4,5,6-hexahydro-2,4-dioxopyrimidinecarboxylate | 0.25 | 89 |
|  | 0.5 | 29 |
|  | 1 | 7 |

Preparation Example

In cases in which the compounds of the present invention are employed as antitumor agent, they may be used, for example, in accordance with the following formulations.

| A. Tablet | | |
|---|---|---|
| (1) | Ethyl 5-fluoro-6-(Z)-furfurylideneaminooxy-1,2,3,4,5,6-hexahydro-2,4-dioxopyrimidine-5-carboxylate | 50 g |
| (2) | Lactose | 30.7 g |
| (3) | Starch | 17 g |
| (4) | Hydroxypropylcellulose | 2 g |
| (5) | Magnesium stearate | 0.3 g |
|  | For 1000 tablets, | 100.0 g |

The ingredients, (1), (2) and (3), were mixed and granulated with the ingredient (4) used as a binder, followed by the addition of the ingredient (5) and compression to produce 1000 tablets (diameter, 6.5 mm, 9R) each weighing 100 mg.

The tablets have a content of the ingredient (1) of 50 mg per tablet.

B. Film-coating tablets

Film-coating tablets were obtained by coating the above tablets with methyl cellulose (5 parts), polyethylene glycol 6000 (1 part) and titanium oxide (0.5 part) in accordance with the conventional procedures.

What we claim is:

1. A compound of the formula

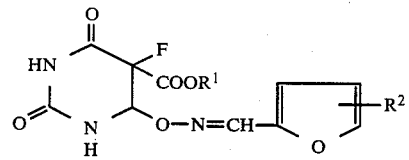

wherein $R^1$ is lower alkyl; $R^2$ is hydrogen or lower alkyl.

2. The compound according to claim 1, wherein $R^1$ is alkyl of 2 to 4 carbon atoms.

3. The compound according to claim 1, wherein $R^2$ is hydrogen.

4. The compound according to claim 1, wherein $R^1$ is alkyl of 2 to 4 carbon atoms and $R^2$ is hydrogen.

5. The compound according to claim 1, wherein $R^1$ is alkyl of 2 to 4 carbon atoms and $R^2$ is methyl.

6. The compound according to claim 1, wherein $R^1$ is ethyl, isobutyl or isopropyl and $R^2$ is hydrogen or methyl.

7. The compound according to claim 1, which is ethyl 5-fluoro-6-(Z)-furfurylideneaminooxy-1,2,3,4,5,6-hexahydro-2,4-dioxopyrimidine-5-carboxylate.

8. The compound according to claim 1, which is ethyl 5-fluoro-6-(E)-furfurylideneaminooxy-1,2,3,4,5,6-hexahydro-2,4-dioxopyrimidine-5-carboxylate.

9. The compound according to claim 1, which is ethyl 5-fluoro-6-[(Z)-5-methylfurfurylideneaminoxy]-1,2,3,4,5,6-hexahydro-2,4-dioxopyrimidine-5-carboxylate.

10. The compound according to claim 1, which is isobutyl 5-fluoro-6-(Z)-furfurylideneaminooxy-1,2,3,4,5,6-hexahydro-2,4-dioxopyrimidine-5-carboxylate.

11. The compound according to claim 1 which is iosbutyl 5-fluoro-6-(E)-furfurylideneaminooxy-1,2,3,4,5,6-hexahydro-2,4-dioxopyrimidine-5-carboxylate.

12. The compound according to claim 1 which is ethyl 5-fluoro-6-[(E)-5-methylfurfurylideneaminooxy]-1,2,3,4,5,6-hexahydro-2,4-dioxopyrimidine-5-carboxylate.

13. The compound according to claim 1 which is 5-fluoro-6-[(Z)-furfurylideneaminooxy]-5-isopropyloxycarbonyl-1,2,3,4,5,6-hexahydro-2,4-dioxopyrimidine.

14. The compound according to claim 1 which is 5-fluoro-6-[(E)-furfurylideneaminooxy]-5-isopropyloxycarbonyl-1,2,3,4,5,6-hexahydro-2,4-dioxopyrimidine.

15. A pharmaceutical composition for inhibiting the growth of tumorous cells which comprises an effective amount of a compound of the formula

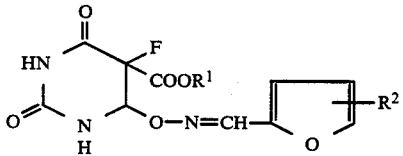

wherein $R^1$ is lower alkyl; $R^2$ is hydrogen or lower alkyl and a pharmacologically acceptable carrier.

* * * * *